US008337833B2

(12) United States Patent
Kraus et al.

(10) Patent No.: US 8,337,833 B2
(45) Date of Patent: Dec. 25, 2012

(54) METHODS OF IMPROVING CENTRAL NERVOUS SYSTEM FUNCTIONING

(75) Inventors: Morey Kraus, Jefferson, MA (US); Seth Finklestein, Needham, MA (US); Paul Clark, Wellesley, MA (US)

(73) Assignees: The General Hospital Corp., Boston, MA (US); ViaCord, LLC, Cambridge, MA (US)

(*) Notice: Subject to any disclaimer, the term of this patent is extended or adjusted under 35 U.S.C. 154(b) by 0 days.

(21) Appl. No.: 12/778,006

(22) Filed: May 11, 2010

(65) Prior Publication Data

US 2010/0322899 A1    Dec. 23, 2010

Related U.S. Application Data

(63) Continuation of application No. 09/698,893, filed on Oct. 27, 2000, now Pat. No. 7,811,557.

(51) Int. Cl.
*A01N 63/00* (2006.01)
*A01N 65/00* (2009.01)
*A61K 35/12* (2006.01)
*A61K 35/14* (2006.01)
*C12N 5/071* (2010.01)

(52) U.S. Cl. ...... 424/93.7; 424/93.1; 424/520; 424/529; 435/366; 435/372

(58) Field of Classification Search ........................ None
See application file for complete search history.

(56) References Cited

U.S. PATENT DOCUMENTS

| | | | |
|---|---|---|---|
| 5,674,750 A | 10/1997 | Kraus et al. | |
| 5,925,567 A | 7/1999 | Kraus et al. | |
| 2002/0028510 A1 | 3/2002 | Sanberg et al. | |

FOREIGN PATENT DOCUMENTS

WO    WO 01/66698 A1    9/2001

OTHER PUBLICATIONS

Hematopoietic Stem Cells, in Stem Cells: Scientific Progress and Future Research Directions. Chapter 5, pp. 43-58, National Institutes of Health, Department of Health and Human Services, Jun. 2001.*
Azizi et al., "Multipotential Stem-Like Cells from Bone Marrow can Differentiate into Macroglia In Vitro and Can Integrate Into Developing Rat Brain," *Am. Society for Neural Transp. & Repair Program and Abstracts* 7:2000.
Cameron et al., "Formation of SNACs by Simulated Microgravity Coculture of Sertoli Cells and NT2 Cells," *Am. Society for Neural Transp. & Repair Program and Abstracts* 7:2000.
Chen et al., "The Potential for the Use of Mononuclear Cells from Human Umbilical Cord Blood in the Treatment of Amyotrophic Lateral Sclerosis in SOD1 Mice," *Journal of Medicine* 31:21-30, 2000.
Chen et al., "Intracerebral Transplantation of Bone Marrow with BDNF After MCAO in Rat," *NeuroPharmacology* 39:711-716, 2000.

Ende et al., "Human Umbilical Cord Blood Cells Ameliorate Huntington's Disease in Transgenic Mice: A Brief Report," *Journal of Medicine* 32:231-240, 2001.
Ende, "Hematopoietic Transplantation by Means of Fetal (Cord) Blood. A New Method," *Virginia Medical Monthly* 99:276-280, 1972.
Ende et al., "Human Umbilical Cord Blood Cells Ameliorate Alzheimer's Disease in Transgenic Mice: A Brief Report," *Journal of Medicine* 32:241-247, 2001.
Grill and Tuszynski, "Axonal Responses to Injury," Chapter 2, in CNS Regeneration: Basic Science and Clinical Advances, Tuszynkski and Kordower, ed. Academic Press, pp. 27-46, 1999.
Jackowski et al., "Neural Injury Repair: Hope for the Future as Barriers to Effective CNS Regeneration Become Clearer," *British J. Neurosurgery* 9:303-317, 1995.
Keene et al., "Phenotypic Expression of Transplanted Human Bone Marrow Derived Multipotent Adult Stem Cells into the Rat CNS," *Am. Society for Neural Transp. & Repair Program and Abstracts* 7:2000.
Kolata, "Researchers Turn Bone Marrow Cells into Nerve Cells," *NY Times on the Web National Science/Health* Aug. 15, 2000.
Kondziolka et al., "Transplantation of Cultured Human Neuronal Cells for Patients with Stroke," *Neurology* 55:467,565-569, 2000.
Kondziolka et al., "Neurotransplantation for Stroke Results From Phase 1 Clinical Trial," *Am. Society for Neural Transp. & Repair Program and Abstracts* 7:2000.
Kraus et al., "Cord Blood Cells Restore Central Nervous System (CNS) Function in a Rat-stroke Model System," *Blood* 96:495a, 2000.
Li et al., "Intra-Carotid Administration of Adult Bone Marrow Cells After Middle Cerebral Artery Occlusion in Adult Rat Brain," *Am. Society for Neural Transp. & Repair Program and Abstracts* 7:2000.
Mahmood et al., "Effects of Transplantation of Bone Marrow Cells on Wistar Rats Following Traumatic Brain Injury," *American Society for Neural Transplantation & Repair Program and Abstracts* 7:2000.
Marciniak et al., "Neural Stem Cells in Combination with Basic Fibro-Blast Growth Factor (BFGF) May Represent a Treatment for Stroke," *American Soc. for Neural Transp. & Repair Program and Abstracts* 7:2000.
Mendez et al., "Simultaneous Intraputaminal and Intranigral Fetal Dopaminergic Grafts in Parkinson's Disease First Clinical Trials," *Am. Society for Neural Transp. & Repair Program and Abstracts* 7:2000.
Moore and Hoskins, "Ex Vivo Expansion of Cord Blood-Derived Stem Cells and Progenitors," *Blood Cells* 20:468-481, 1994.
Ren et al., "Time Window of Intracisternal Osteogenic Protein-I in Enhancing Functional Recovery After Stroke," *NeuroPharmacology* 39:860-865, 2000.
Ren et al., "Co-Administration of Neural Stem Cells and BFGF Enhances Functional Recovery Following Focal Cerebral Infarction in Rat," *Soc. Neurosci.* 26:2291, 2000.

(Continued)

*Primary Examiner* — Anne-Marie Falk
(74) *Attorney, Agent, or Firm* — Clark & Elbing LLP; Todd Armstrong

(57) ABSTRACT

Methods of causing an improvement in central nervous system function are provided. The methods include administering an aliquot of stem cells to the patient, the cells being derived from blood, e.g., umbilical cord blood. In some cases a growth factor is administered with the cells.

16 Claims, 10 Drawing Sheets

OTHER PUBLICATIONS

Rosu-Myles et al., "Characterization of Chemokine Receptors Expressed in Primitive Blood Cells During Human Hematopoietic Ontogeny," *Stem Cells* 18:374-381, 2000.

Sanchez-Ramos et al., "Adult Bone Marrow Stromal Cells Differentiate into Neural Cells In Vitro," *Am. Society for Neural Transp. & Repair Program and Abstracts* 7:2000.

Steindler et al., "Stem Cells in the Adult Human Brain: Their Molecular Cell Biology Potential Use in Cell Replacement and Involvement in Neoplasia," *Am. Soc. for Neural Transp. & Repair Program and Abstracts* 7:2000.

Stem Cells: Scientific Progress and Future Research Directions. Executive Summary, pp. ES-1 to ES-10, and Chapters 1 and 2, pp. 1-9. Department of Health and Human Services, Jun. 2001. http://www.nih.gov/news/stemcell/scireport.htm.

Stroemer et al., "Implantation Site of Stem Cells in MCAO Rats Influences the Recovery on Different Behavioral Tests," *Am. Soc. for Neural Transp. & Repair Program and Abstracts* 7:2000.

Willing et al., "Neural Stem Cells Transplanted in the Middle Cerebral Artery Occlusion Model of Stroke," *American Society for Neural Transplantation & Repair Program and Abstracts* 7:2000.

Zhao et al., "Transplanted Human Bone Marrow Derived Adult Stem Cells Survive and Improve Functional Outcome in Rat Model of Cortical Ischemic Brain Injury," *Am. Society for Neural Transp. & Repair Program and Abstracts* 7:2000.

Pages from Layton Bioscience Inc. Website http://www.laytonbio.com.whatsnew.htm.

Pages from Website http://www.diacrin.com/new.htm.

Pages from Proneuron Pipeline Website http://www.proneuron.com.products.html.

Pages from Stem Cells, Inc. Website http://www.corporate-ir.net.ireye.ir_site.html.

Pages from ReNeuron Website http://www.reneuron.com_Company.html.

Meier et al., "Spastic Paresis After Perinatal Brain Damage in Rats is Reduced by Human Cord Blood Mononuclear Cells," *Pediatric Research*. 59(2): 244-249, 2006.

\* cited by examiner

METHODS OF IMPROVING CENTRAL NERVOUS SYSTEM FUNCTIONING

CROSS REFERENCE TO RELATED APPLICATIONS

This application is a continuation of, and claims priority from, U.S. patent application Ser. No. 09/698,893, filed Oct. 27, 2000 now U.S. Pat. No. 7,811,557 (allowed), which is incorporated herein by reference in its entirety.

TECHNICAL FIELD

This invention relates to methods of improving central nervous system functioning.

BACKGROUND

The central nervous system is a complex system of tissues, including cells, fluids and chemicals that interact in concert to enable a wide variety of functions, including movement, navigation, cognition, speech, vision and emotion. Unfortunately, a variety of debilitating malfunctions of the central nervous system may occur and disrupt some or all of these functions. These malfunctions are broad in range and include, for example, missing genetic elements, e.g., genetic diseases such as Tay-Sachs; malfunctioning cellular processes, e.g., Parkinson's Disease; trauma, e.g., head injury; degenerative diseases, e.g., Alzheimer's Disease; and damage due to lack of oxygen, e.g., caused by stroke or asphyxiation.

Typically, treatments for restoring central nervous system function after damage by the above malfunctions have been limited to drugs, and to adaptive or behavioral therapies. These approaches are generally limited in their ability to reverse damage (or stop degeneration) and restore normal function.

Recent research has explored the possibility of using cells to restore function to the central nervous system. Data using animal models suggests that cell implantation or transplantation may be an effective means for restoring central nervous system function after damage. Cells that have been used in this research have included various nonhematopoietic precursor cells, for example, fetal or embryonic neural cells from porcine and human sources (see, e.g., Nairne, S. P., *Animal-to-Human transplants; the ethics of Xenotransplantation.* London: Nuffield Council of Bioethics, 1996); immortalized fetal neural cells (Ren et al., *Co-Administration of Neural Stem Cells and bFGF Enhances Functional Recovery Following Focal Cerebral Infarction in Rat*, Soc. Neurosci. Abstr., 26:2291, 2000); mesenchymal bone marrow stem and progenitor cells (Chen et al., *Intracerebral Transplantation with Cultured Bone Marrow Stroma Cells after MCAO in Rats*, American Society for Neural Transplantation & Repair, Program and Abstracts, Volume 7: 2000, A-3) including multipotent adult stem cells (see, e.g., Keene et al., *Phenotypic Expression of Transplanted Human Bone Marrow-Derived Multipotent Adult Stem Cells into the Rat CNS*, American Society for Neural Transplantation & Repair, Program and Abstracts, Volume 7: 2000, 6-3); murine neural stem cells (Marciniak, *Neural Stem Cells, In Combination with Basic FibroBlast Growth Factor (bFGF) May Represent a Treatment/or Stroke*, supra, A-I), including immortalized murine neuroepithelial stem cells (Modo et al., *Implantation Site of Stem Cells in MCAD Rats Influences the Recovery on Different Behavioral Tests*, supra, 8-2); adult mouse and human neural stem and progenitor cells (see, e.g., Steindler et al., *Stem Cells in the Human Brain*, supra, 8-3); fetal mesencephalic cells (Mendez et al., *Simultaneous Intraputaminal and Instranigral Fetal Dopaminergic Grafts in Parkinson's Disease: First Clinical Trials*, supra, 5-3); testis-derived Sertoli cells (Cameron et al., *Formation o/SNACs by Simulated Microgravity Coculture of Sertoli Cells and NT2 Cells.* supra, C-), and crude bone marrow extract (Mahmood et al., *Effects of Transplantation of Bone Marrow Cells on Wistar Rats Following Traumatic Brain Injury*, supra, A-4). To overcome the lack of availability of many of these types of cells, researchers have even resorted to studying the possibility of administering cancer cells such as teratacarcinomal cells (Kondziolka et al., *Transplantation of Cultured Human Neuronal Cells/or Patients with Stroke*, Neurology 2000, 55: 565-569), despite the inherent dangers of the use of cancerous cells. Some research into cellular therapies has reached the clinical stage. Generally, the cells that have been used in the research described above pose potential hazards to patients, and/or are difficult to obtain.

SUMMARY

The present invention features methods of enhancing recovery of central nervous system function by administering cells derived from blood, e.g., cells derived from cord blood. By "cord blood", we mean blood that is derived from the placenta or umbilical cord around the time of the birth of a human infant. Advantageously, there is a readily available supply of such cells, without resort to fetal or embryonic sources or to harvesting the patient's own brain cells. For example, cord blood cells are currently banked for autologous or allogeneic administration in other applications. As a result, these cells need not be immortalized, and therefore there is a reduced risk of possible cancerous outgrowths or other detrimental complications that may result from the use of immortalized cells. Because these cells are primary cells, they also are less likely to be carcinogenic or cause other related problems. Also, the use of autologous or immunologically matched cord blood cells reduces the risk of rejection.

Moreover, in some cases, e.g., if a large supply of cord blood is not readily available, a suitable cell population can be obtained using a relatively small sample of cord blood or other source of relatively undifferentiated precursor cells, e.g., as described in U.S. Pat. Nos. 5,674,750 and 5,925,567, the entire disclosures of which are incorporated herein by reference.

A method of causing an improvement in function of the central nervous system of a subject, comprising administering to the subject an aliquot of cells derived from umbilical cord blood.

In one aspect, the invention features a method of causing an improvement in a function of the central nervous system of a subject, comprising administering to the subject an aliquot of cells derived from blood, the aliquot containing stem cells.

In another aspect, the invention features a method of causing an improvement in a function of the central nervous system of a subject, comprising administering to the subject an aliquot of cells derived from blood and a growth factor.

Implementations of the invention may include one or more of the following features. The cells are derived from umbilical cord blood. The cells are derived from peripheral blood. The method further includes obtaining the aliquot of cells by separating a desired cell population from the cord blood. The growth factor is selected from the group consisting of oncostatin M and growth factors from the following families: FGF, neurotrophin, IGF, CNTF, EGF, TGF-beta, LIF, interleukins, PDGF and VEGF. The method further includes obtaining a sample of cells and purifying the sample to obtain the aliquot.

The method further includes obtaining a sample of cells and expanding at least a selected population of cells in the sample ex vivo to obtain the aliquot. The aliquot of cells includes allogeneic cells. Alternatively, or in addition, the aliquot of cells includes autologous cells. The improvement results in recovery from a central nervous system trauma, repair of central nervous system damage or disease, and/or regeneration of central nervous system tissue. The improvement includes measurable stroke recovery. The improvement is the result of stroke repair. The improvement results from tissue regeneration after a stroke. The improvement results from a genetic element contained in the administered cells. The genetic element is endogenous to the administered cells. The genetic element has been exogenously added to the administered cells. The improvement includes head trauma recovery and/or repair. The improvement results from tissue regeneration after head trauma. The cells are administered intercerebrally. The cells are CD 34+/−, Lin− cells or precursor cells. The cells are characterized as: $CD2^-$, $CD3^-$, $CD14^-$, $CD16^-$, $CD19^-$, $CD24^-$, $CD56^-$, $CD66b^-$, glycophorin $A^-$, $flk-1^+$, $CD45^+$, $CXCR4^+$, $MDR^+$. The improvement results from treatment of one of the following diseases: Parkinson's Disease, Alzheimer's Disease, Huntington's Disease, ALS, MS, Tay-Sacks, and cerebral palsy. The method further includes administering to the subject a cell differentiation factor or a neural guidance molecule.

In a further aspect, the invention features a method of causing an improvement in central nervous system function of a patient including (i) obtaining an aliquot containing a predetermined target population of cells by (a) introducing a starting sample of cells into a growth medium; (b) causing cells of the predetermined target population to divide; and (c) concurrently with, intermittently during, or following step (b), contacting the cells in the growth medium with a selection element, so as to select cells of the target population from other cells in the growth medium; and (ii) administering the aliquot to the patient.

The selection element may include a plurality of selective binding molecules with affinity either for target cells or for a first population of non-target cells. The starting sample may be cord blood or be derived from cord blood. The aliquot of cells may include CD 34+/−, Lin− cells. Expansion may be clonogenic.

The term "blood", as used herein, refers to peripheral, fetal and cord blood, and is not meant to include bone marrow.

The phrase "blood-derived cells" refers to relatively undifferentiated cells, and is not intended to include differentiated lymphoid cells such as T or B cells.

Other features and advantages of the invention will be apparent from the description and drawings, and from the claims.

DESCRIPTION OF DRAWINGS

FIG. 2 is a highly enlarged diagrammatic view illustrating a method of positive selection of a target cell. FIG. 3 is a highly enlarged diagrammatic view illustrating a method of negative selection of a non-target cell.

DETAILED DESCRIPTION

Figure 1:
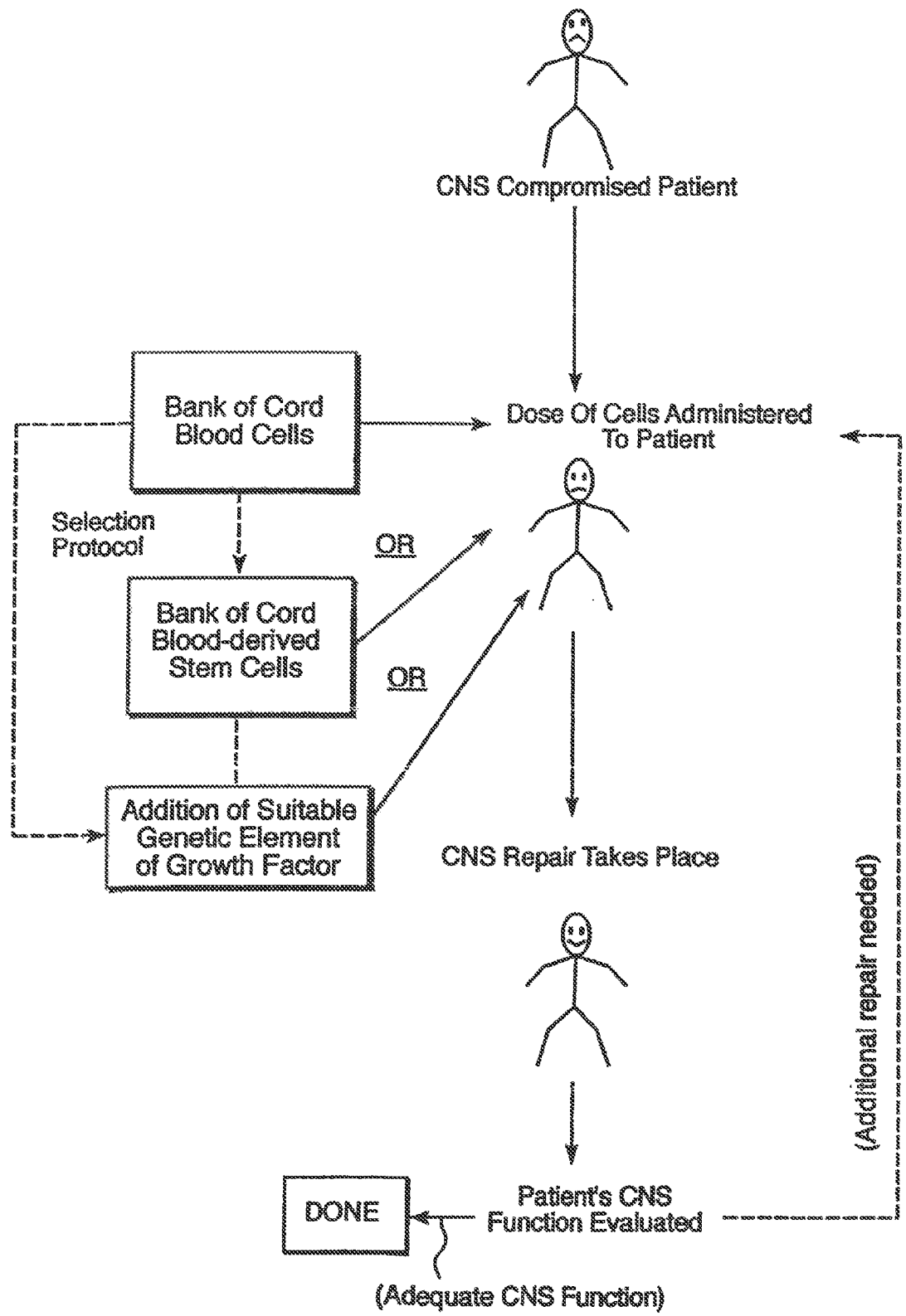
FIG. 1 is a diagram illustrating a method of treating a CNS-compromised patient according to one aspect of the invention.

A preferred method of treating a human patient suffering from CNS impairment or damage is shown schematically in FIG. 1. According to this method, the patient receives a therapeutic dose of blood-derived cells. The cells may be obtained, for example, from a bank of cord blood cells. Alternatively, cord blood cells can be put through a selection procedure, e.g., as described below and in U.S. Pat. No. 5,925,567, to select for CD 34+/−, Lin− cells, and a relatively concentrated sample of these cells may be administered. If desired, the population of CD 34+/−, Lin− cells may be expanded prior to administration to the patient, as described in U.S. Pat. No. 5,925,567. An adjuvant, e.g., a growth factor or genetic element, can be added to the cord blood cells or CD 34+/−, Lin− cells, or co-administered therewith, if desired.

After the cells are administered to the patient, e.g., using the methods described below, the CNS function of the patient is tested after a period of time, e.g., 90 days, to determine the extent of recovery of function that has occurred. If recovery is determined to be inadequate, a further dose of cells will be administered and the evaluation process will be repeated. If desired, CNS function can be tested more frequently, e.g., after 30 days and, if treatment is repeated, periodically during such further treatment, in order to monitor effectiveness of treatment and degree of improvement in CNS function.

The cells can be administered to a patient using any suitable technique. One suitable technique is intracerebral injection, either directly into the brain (intraparenchymally) or into the spinal fluid (intraventricularly or intracisternally). The cells are generally carried in a pharmaceutically acceptable liquid medium. Administration can be repeated or performed continuously (e.g., by a continuous infusion into the spinal fluid). Multiple administrations are generally spaced at least 2-7 days apart.

If the cells are to be injected into the brain, the patient's head is immobilized in a standard stereotactic frame, and the site of administration of the cells is located, e.g., by standard CT or MRI scan. A small-bore hole is drilled in the skull, and the cells are injected into the desired location using a syringe.

Suitable dosages of cells will vary depending on the amount of CNS damage or deterioration that the patient has sustained, the weight of the patient, and other factors. Generally, the dosage may range from about 100,000 to 1,000,000,000 cells per administration, typically from about 1,000,000 to 10,000,000 cells.

Preferably, the cells administered are non-fetal, non-embryonic and are derived from blood. Suitable sources include fresh cord blood, CD 34+/−, Lin− cells separated from cord blood, and CD 34+/−, Lin− cells derived by expanding cells selected from cord blood.

In the case of a selected and/or expanded population, the cells are preferably CD 34+/−, Lin− cells or precursor cells that are characterized as: $CD2^-$, $CD3^-$, $CD14^-$, $CD16^-$, $CD19^-$, $CD24^-$, $CD56^-$, $CD66b^-$, glycophorin $A^-$, $flk-1^+$, $CD45^+$, $CXCR4^+$, $MDR^+$.

Figure 2:
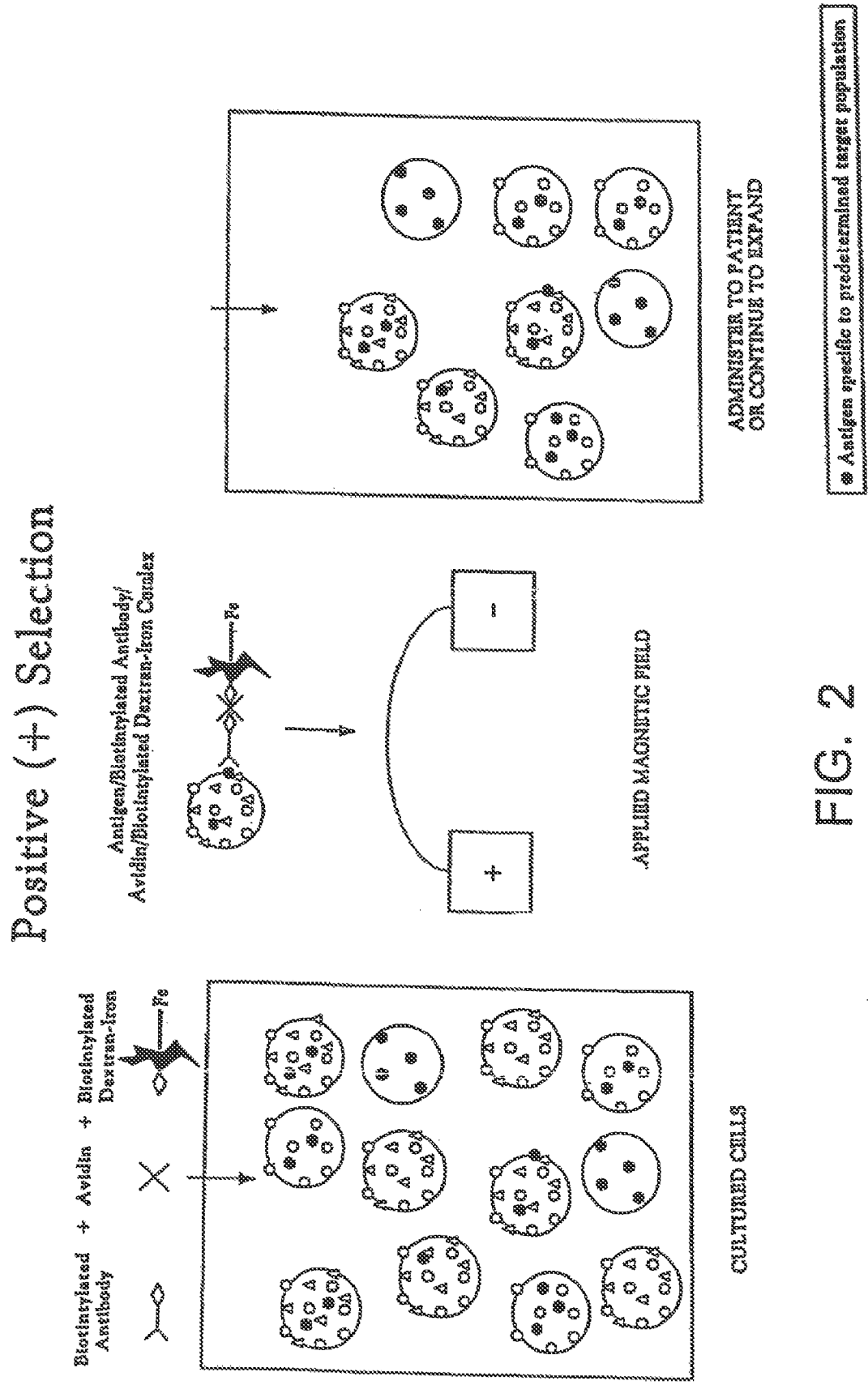
FIGS. 2 and 3 illustrate methods of obtaining cells suitable for use in the invention by selection.
Figure 3:
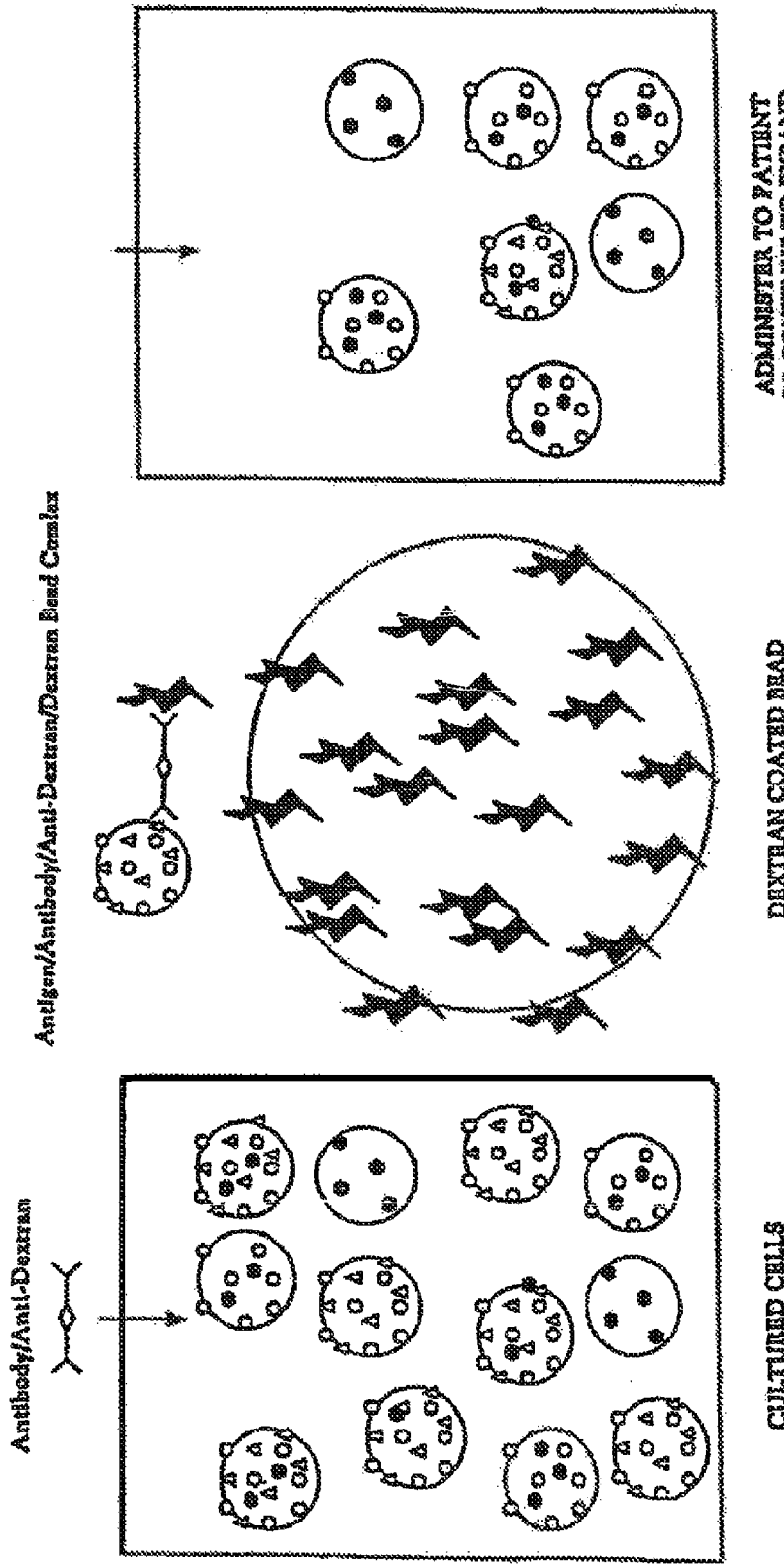

Suitable procedures for separating CD 34+/−, Lin− cells from cord blood, and expanding the separated population, are described in U.S. Pat. No. 5,925,567 and summarized below. Separation/Expansion Procedures FIGS. 2 and 3 illustrate suitable selection procedures. According to these procedures, cells of a desired target population may be substantially continuously proliferated by providing a system containing a nutrient medium in which cell proliferation can occur, and selecting cells of the target population from non-target cells in the system, concurrently with proliferation, intermittently during proliferation or following proliferation. Cell proliferation and cell selection can be carried out using an almost infinite variety of different techniques and settings, of which only a few are described below by way of example. Many other techniques will be readily perceived by those skilled in the art.

All of the preferred techniques, however, are based on the concepts of positive selection (providing a selection element having an affinity for ("selecting") target cells), and negative selection (providing a selection element having an affinity for ("selecting") non-target cells). These two techniques used alone or in combination, allow unwanted cells to be removed from the system and target cells to be harvested whenever desired.

An example of a positive selection technique is illustrated diagrammatically in FIG. 2. Briefly, one or more biotintylated antibodies, specific for the target cells, and avidin are sequentially introduced into the system. After a specified incubation time any biotintylated antibody and avidin which have not formed a complex with the target cells are rinsed away. Biotintylated dextran-iron is then added to the cell suspension. The biotintylated dextran-iron reacts with the AvidinBiotintylated Antibody/Antigen Complex to form a larger complex containing the biotintylated dextran-iron. This suspension is then passed through a magnetic field. Positively selected cells remain in the magnetic field while cells which do not have the iron conjugated complex are removed. After capture and rinsing, the magnetic field is removed and the positively selected predetermined target population is returned to the nutrient medium.

An example of a negative selection technique is illustrated diagrammatically in FIG. 3. Briefly, one or more anti-dextran conjugated antibodies specific for a predetermined population which is not of the predetermined target population is introduced into the culture. After a specified incubation time the cell suspension is passed through a column containing dextran coated glass beads. An Antigen/Antibody/Anti-dextran/Dextran/Bead Complex forms, removing cells not of the predetermined target population from the nutrient medium. The predetermined target population is collected downstream and returned to the nutrient medium.

Clearly, many other techniques could be utilized for both positive and negative selection, as long as the desired affinity is provided by the selection element.

The selection element can be simply the selection molecule itself, or can include other components, e.g., a solid support onto which the selection molecule is bound. The solid support can be formed of a material that will aid in performing the selection or in maintaining the selection molecules in a desired position or introducing and removing them from the system. For example, as described above with reference to FIG. 2, the selection molecule can be bound to iron or other magnetic particles to allow the selected cells to be easily removed from the system by application of a magnetic field and then collected by removal of the magnetic field. Alternatively, the selection molecules can be bound onto the wall of a vessel containing the nutrient medium, or of a chamber through which the nutrient medium flows during the method. Glass or other inert, impermeable beads can also be used as a solid support, as will be discussed in detail below. If beads or other particles are used, they can be provided in a packed configuration, through which the nutrient medium flows, or can be introduced into the system in a loose form, suspension, or in any desired type of array. As will be readily understood, a wide variety of other solid supports can be used.

Adjuvants

Various adjuvants may be administered to the patient to further enhance recovery of CNS function. The aliquot of cells may include various adjuvants, or adjuvants may be co-administered with the cells. Suitable adjuvants include neural stimulants such as growth factors and neurotransmitters. Genetic elements may also be used as adjuvants, as will be discussed below.

Suitable growth factors are discussed in co-pending application U.S. Ser. No. 60/149,561, filed Aug. 18, 2000, the disclosure of which is incorporated by reference herein. Suitable growth factors include members of the fibroblast growth factor (FGF) family, e.g., basic FGF, acid FGF, the hst/Kfgf gene product, FGF-5, or int-2; the neurotrophin family, e.g., nerve growth factor (NGF), brain-derived neurotrophic factor (BDNF), neurotrophin 3 (NT3), or neurotrophin 4/5 (NT4/5); the insulin-like growth factor family, including IGF-1 and IGF-2; the ciliary neurotrophic growth factor (CNTF) family; the EGF family, including EGF, TGF-alpha, and HB-EGF; the TGF-beta family, including TGFbeta and members of the BMP subfamily; leukemia inhibitory factor (LIF); oncostatin M; interleukins such as IL-II; members of the platelet-derived growth factor (PDGF) family; and the VEGF family. Bioactive fragments, analogues and active fragments of the above-mentioned growth factors may also be used.

The preferred dosage of the growth factor(s) will depend upon the result desired and the route of administration. The growth factor(s) may be administered with the cells, or by a different route, including directly into the brain (intracerebrally), systemically (e.g., intravenously) or into the spinal fluid (intracisternally or intracerebroventricularly). If administered directly into the brain or into the spinal fluid, the preferred total amount of growth factor per administration is generally from about 0.001 to 1000 mg, preferably about 0.01 to 100 mg. If administration is systemic, the dosage will generally be based on the patient's body weight, with typical dosages being from about 0.001 to 100 mg/kg, preferably about 0.01 to 10 mg/kg.

Suitable neurotransmitters include neurotransmitter agonists or antagonists such as Prozac, amphetamines, Ritalin, and tricyclic antidepressants such as Elavil. These compounds act as neural stimulants, and have well-established effects on the brain.

Administration of a genetic element may enhance recovery of a patient from a genetic disease such as Tay-Sachs. For example, if a patient is suffering from a disease resulting from the lack of function or dysfunction of a naturally occurring protein, as a result of a gene mutation or genetic flaw, an exogenous gene may be installed on the cells to be administered to the patient. This is generally necessary when the cells that are administered are autologous cells. If allogeneic cells, e.g., immunologically matched cells, are administered to the patient, it is generally not necessary to install an exogenous gene, as the necessary gene would typically be present endogenously and would function properly. However, in some cases it may be desirable to install an exogenous gene in this case as well.

Other adjuvants may be administered, as discussed in co-pending application U.S. Ser. No. 60/149,561, e.g., cell differentiation factors such as retinoic acid, neural guidance molecules such as semaphorins, netrins, neuropilins and ephrins, and physical treatments such as transcranial magnetic stimulation.

Evaluating CNS Function

Advantageously, the methods of the invention generally result in a measurable improvement in CNS function, e.g., measurable stroke recovery. Tests that may be used to evaluate stroke recovery in humans include global functional and neurological outcome scores (Modified Rankin Scale, NIH stroke scale, and Barthel Index); specialized tests of neurological function (Fugl-Meyer Scale of motor functioning; neuropsychological test battery) and other tests, e.g., the tests described in U.S. Pat. No. 5,885,231, the disclosure of which is incorporated by reference herein. Other tests that may be used to evaluate CNS function are well known in the neurological field.

EXAMPLE

Stem cells (CD 34+/−, Lin− cells) were selected from a sample of fresh cord blood cells using the procedure described in Example 5 of U.S. Pat. No. 5,925,567, incorporated by reference above.

Figure 4A:
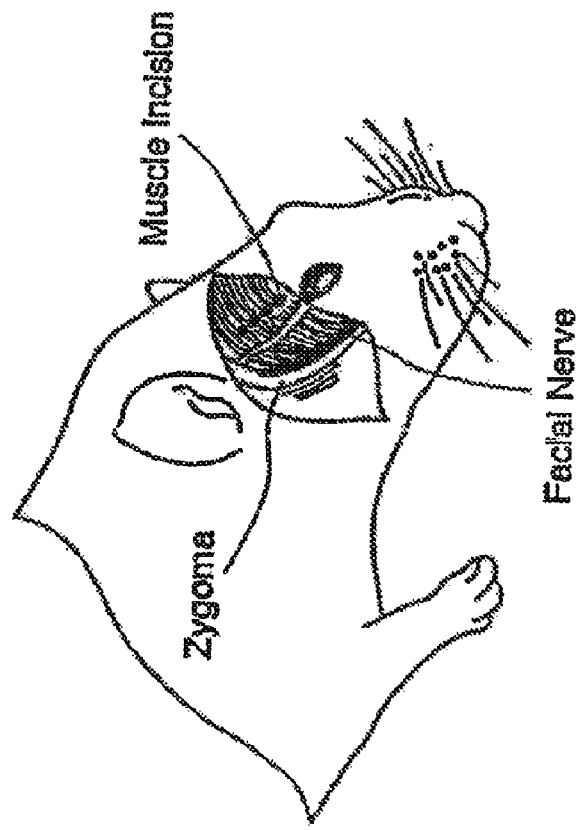
FIG. 4A is a schematic perspective view showing a rat that has been prepared for a stroke model.
Figure 4B:
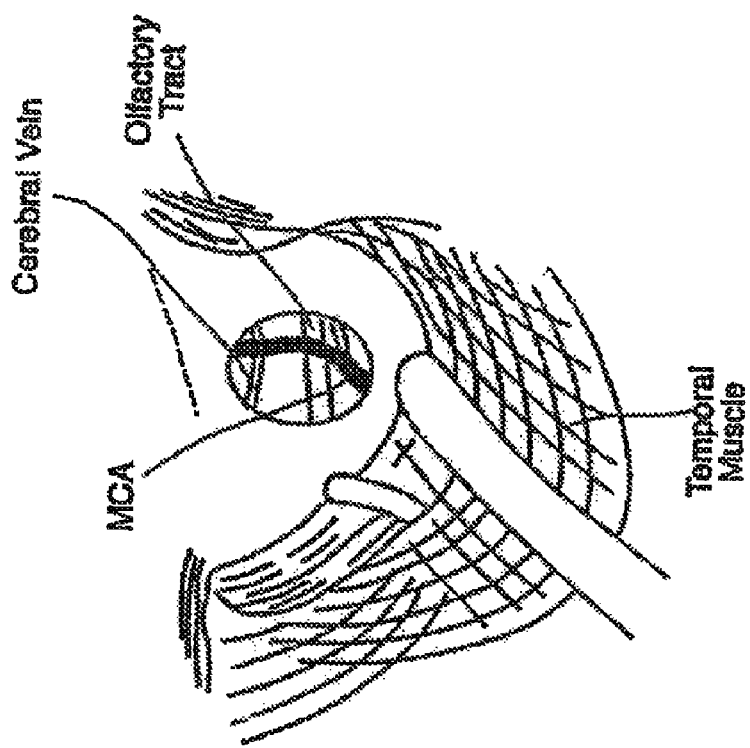
FIG. 4B is a schematic diagram of an occlusion of the proximal MCA of the rat.

20 male Sprague Dawley rats, each weighing 300-350 grams, were anesthetized with a 2% halothane with nitrous oxide/oxygen mixture (2:1), and subjected to a MCA occlusion, using a Modified Tamura model (see FIGS. 4A and 4B). This stroke model has been described in the literature (see, e.g., Kawamata, T., et al., *Intracisternal Basic Fibroblast Growth Factor (bFGF) Enhances Functional Recovery and Upregulates the Expression of a Molecular Marker of Neuronal Sprouting Following Focal Cerebral Infarction*. Proc. Natl. Acad. Sci., 1997.94: p. 8179-8184).

Figure 5:
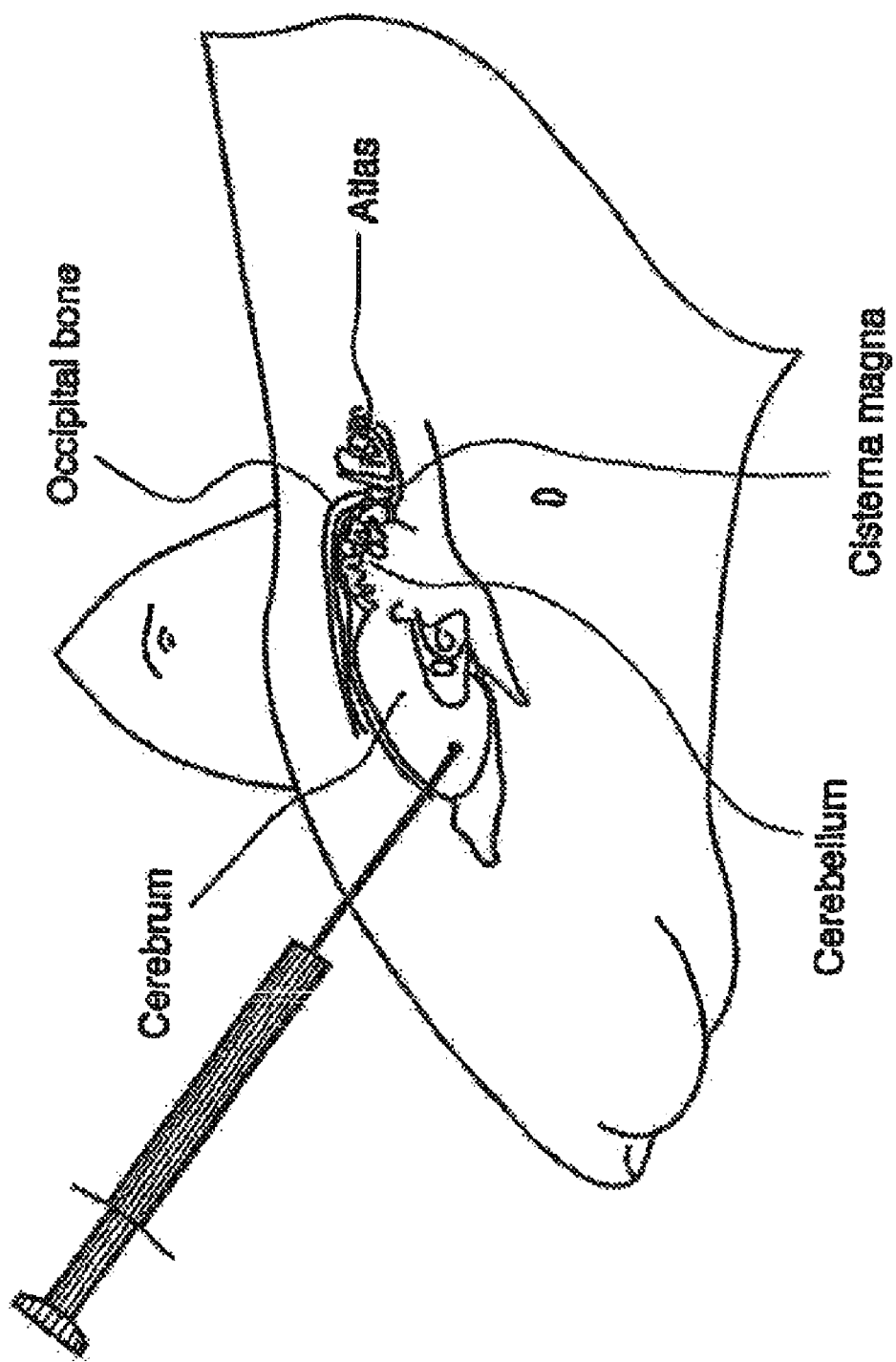
FIG. 5 is a schematic diagram showing a rat receiving an intraparenchymal administration of stem cells.
Figure 6:
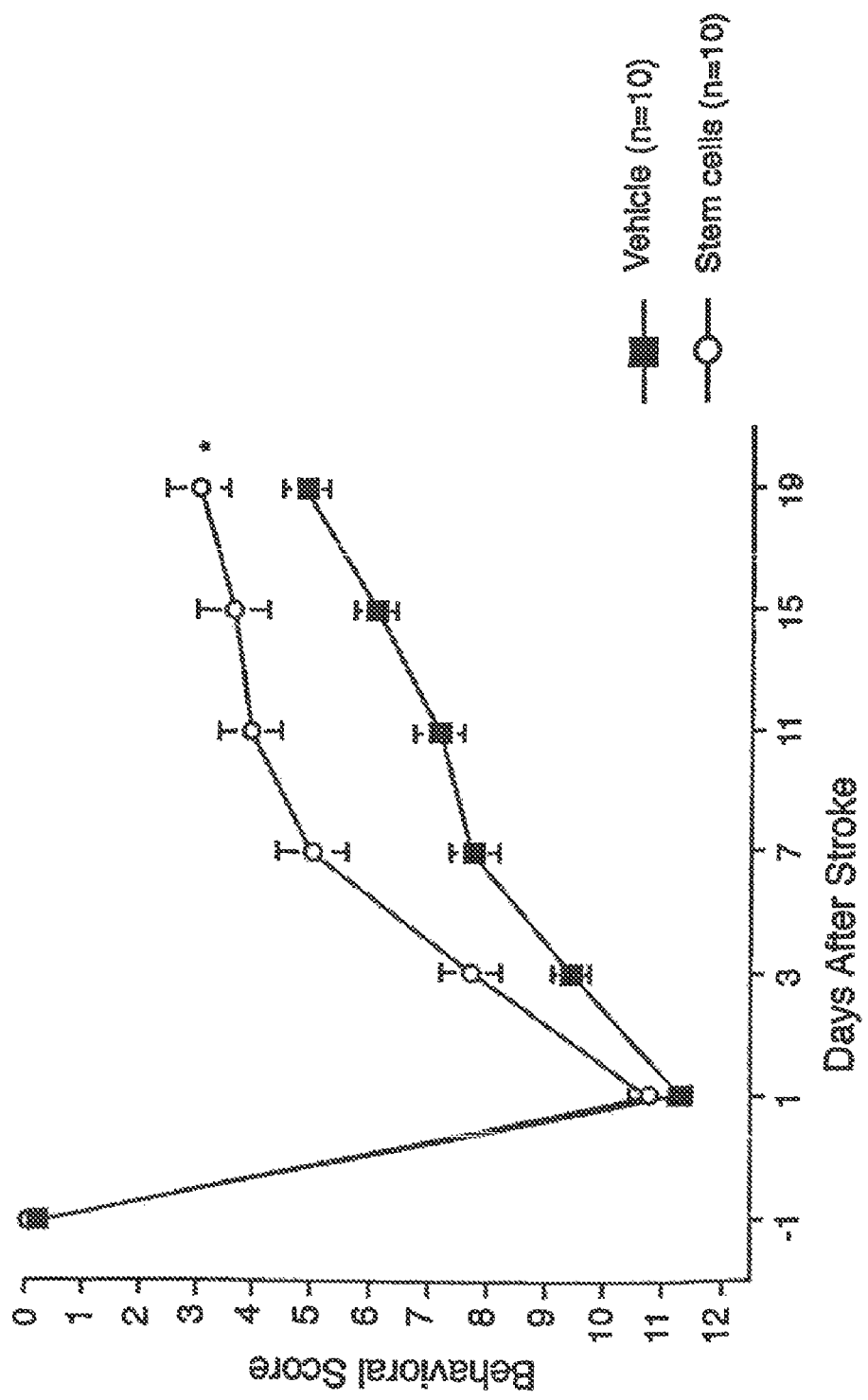
FIGS. 6-10 are graphs showing the results of behavioral tests performed on stroke model rats.
Figure 7:
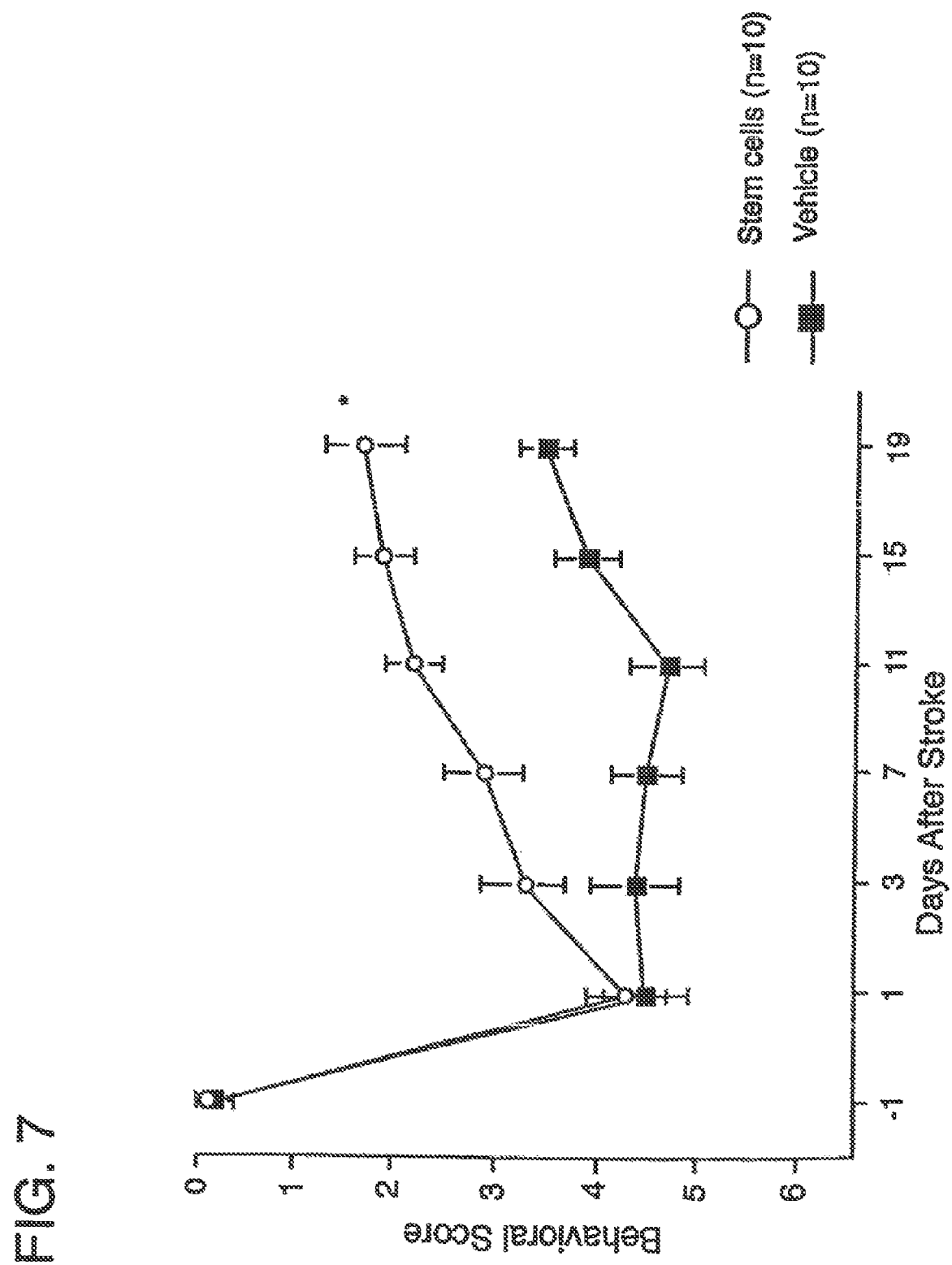
Figure 8:
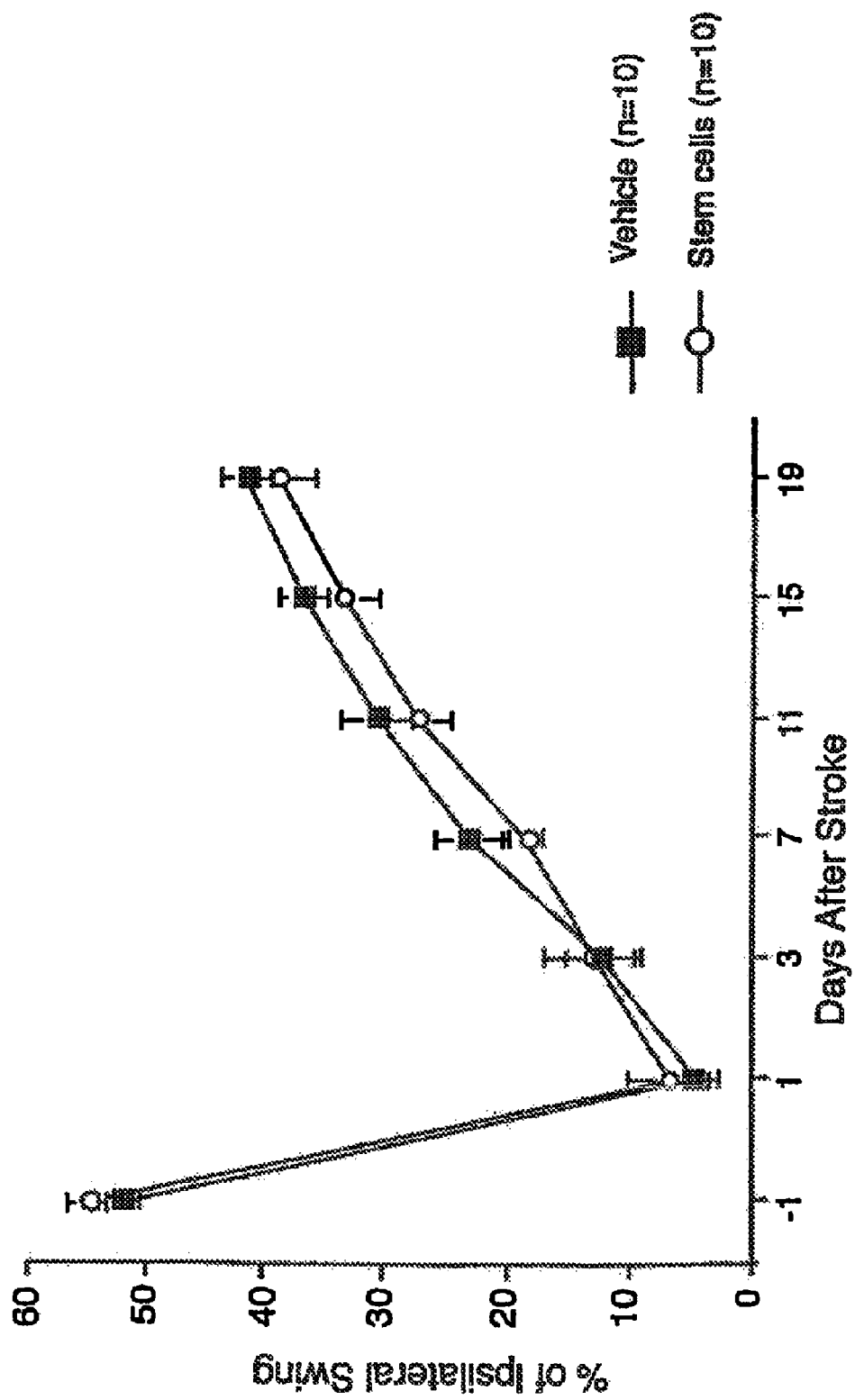
Figure 9:
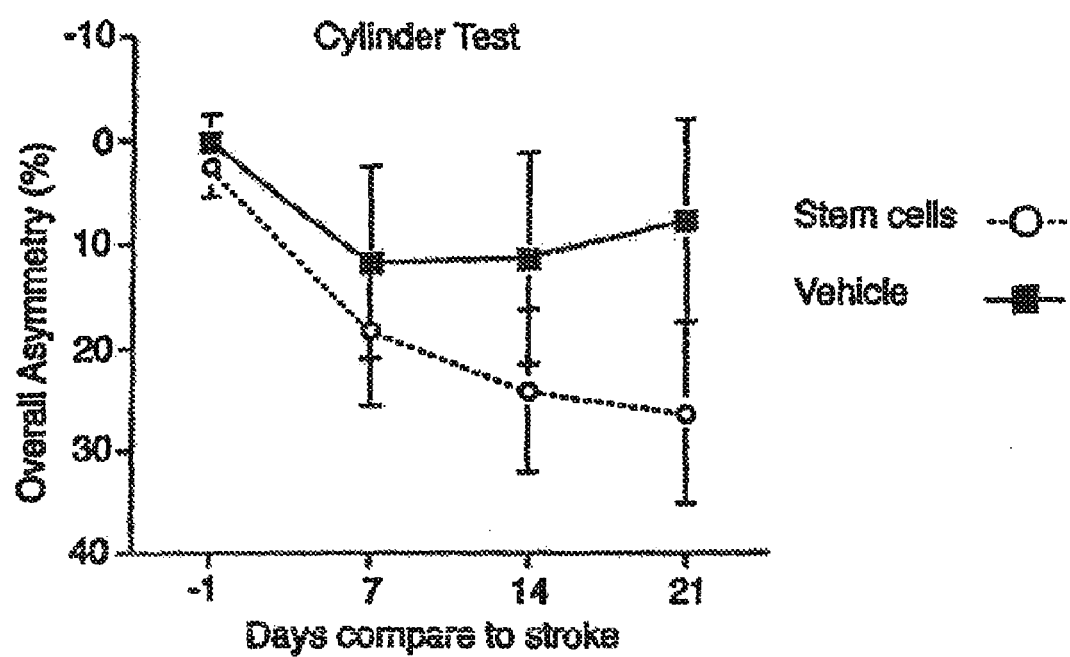
Figure 10:
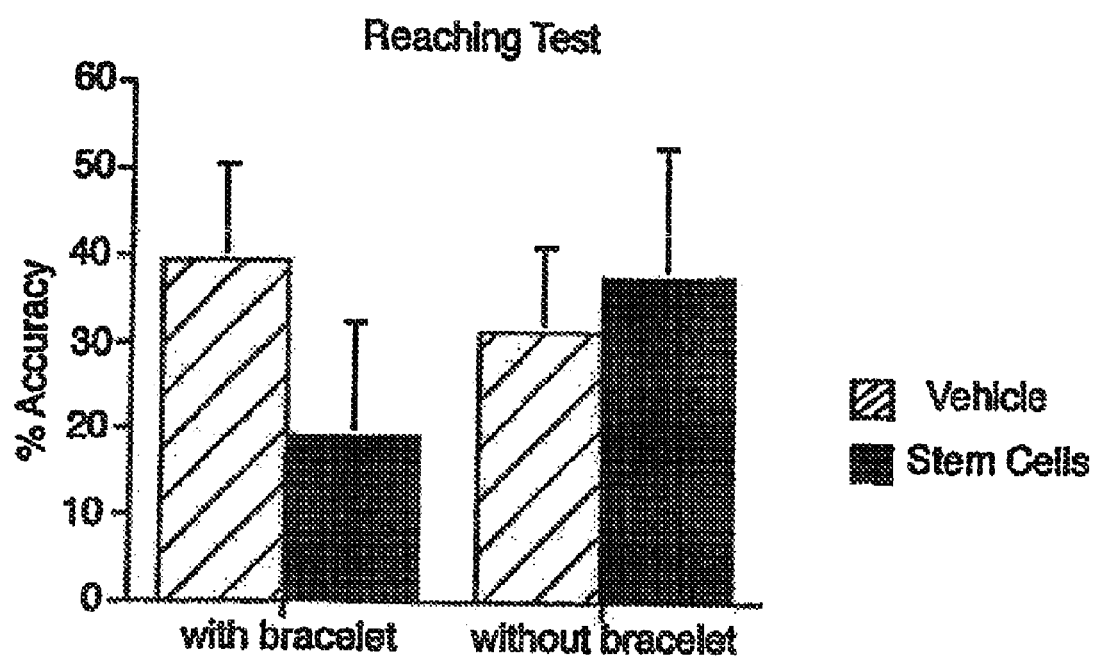

The rats received cefazolin sodium i.p. (40 mg/kg) one day before surgery and immediately following surgery. 24 hours after the occlusion, all of the rats received an injection directly into the brain tissue surrounding the stroke (FIG. 5). 10 of the rats were injected with 1,000,000 stem cells each; the other 10 rats were injected with physiological buffered saline (PBS) vehicle. After injection, the rats were given cyclosporin i.p. each day (10 mg/kg), The rats were tested 3 days after the occlusion surgery, and then every 4 days thereafter for the next 21 days to determine their central nervous system function. The rats had also been tested, using the same tests, one day prior to the occlusion surgery (day −1). They were tested using several behavioral tests, described below. For these tests, rats are handled for 10 min. each day for seven days before stroke surgery.

The forelimb and hindlimb placing tests, described briefly below, are described in further detail in Kawamata et al., supra. For the forelimb placing test, the examiner holds the rat close to a table top and scores the rat's ability to place the forelimb on the table top in response to whisker, visual, tactile, or proprioceptive stimulation. Similarly, for the hindlimb placing test, the examiner assesses the rat's ability to place the hindlimb on the table top in response to tactile and proprioceptive stimulation. Separate subscores are obtained for each mode of sensory input and added to give total scores (for the forelimb placing test: 0=normal, 12=maximally impaired; for the hindlimb placing test: 0=normal; 6=maximally impaired).

The body swing test (described in detail in Borlongan et al., *Transplantation of Cryopreserved Human Embryonal Carcinoma-derived Neurons (NT2N Cells) Promotes Functional Recovery in Ischemic Rats*, Exp. Neurol., 1998. 149: p. 310-321) has been used to examine side preferences after stroke. The animal is held approximately 1 inch from the base of its tail. It is then elevated to an inch above a surface of a table. The animal is held in the vertical axis, defined as no more than 10° to either the left or the right side. A swing is recorded whenever the animal moves its head out of the vertical axis to either side. Before attempting another swing, the animal must return to the vertical position for the next swing to be counted. Thirty total swings are counted. A normal animal typically has an equal number of swings to either side. Following focal stroke, the animal tends to swing to the contralateral side. There is a slow spontaneous recovery of body swing during the first month after stroke.

Two other tests were conducted, the cylinder test and the paw reaching test. The cylinder, or "spontaneous limb" test (described in detail in Jones, T. A. & Schallert, T., *Use-dependent Growth of Pyramidal Neurons After Neocortical Damage*, J. Neurosci., 1994. 14: p. 2140-2152), examines the forelimb side preference of animals as they rear up in a narrow glass cylinder. Animals are placed in a narrow Plexiglas cylinder (18×30 cm) and videotaped for 5 min (or for a minimum number of movements) on the day before stroke surgery and at weekly intervals thereafter. Videotapes are then scored for the number of spontaneous movements made by each forelimb to initiate rearing, to land on or to move laterally along the wall of the cylinder, or to land on the floor after rearing. The mean number of spontaneous movements of each forelimb is then expressed as an asymmetry score (total contralateral forelimb use−total ipsilateral forelimb use)/total forelimb use). Before stroke, animals tend to use both forelimbs equally. After stroke, there is a preference for the unimpaired (ipsilateral) forelimb. This asymmetry recovers spontaneously to a partial degree during the first month after stroke.

The paw reaching test (described in detail in Kolb et al., *Nerve Growth Factor Treatment Prevents Dendritic Atrophy and Promotes Recovery of Function After Cortical Injury*, Neuroscience, 1997.76: p. 1139-1151), measures the dexterity of the forepaws in reaching through the bars of a cage to grab and eat food pellets. Animals are food-deprived (allowing 15 g regular food per day) before the training and testing dates. The animals are placed in the test cages (23×30×13 cm) with floors and wall constructed of 2 mm bars, 9 mm apart edge to edge. A 8 cm wide and 6 cm deep tray, containing chocolate flavored pellets (45 mg/each), is mounted on one wall of the cage. The rats are required to extend a forelimb through the gap in the bars, grasp and retract the food. The tray is 0.5 cm apart from the cage so that the rats cannot scrape the food into the cage. Rats are trained for 10 days using both forepaws before stroke surgery. After stroke surgery, they are trained again for 5 days using only the impaired (contralateral) paw. This is done by placing a bracelet on the intact paw, which does not allow it to reach through the bars of the cage. Then, animals are videotaped for 5 min. with the bracelet on, and 5 min. with the bracelet off. The total number of "reaches" and "hits" (successful grabbing and eating of food pellet) are recorded for each interval.

The results of these behavioral tests are shown in FIGS. 6-10. The asterisks in FIGS. 6 and 7 indicate that data in the stem cell groups were different from the vehicle groups by $p<0.05$ by two-way ANOVA (treatment X time). The lack of asterisks in FIGS. 8-10 indicate that there were no significant differences.

A statistically significant difference was observed between the rats that received stem cells and the rats that received the vehicle in the forelimb and hindlimb placing tests, with the rats that received stem cells showing significantly better recovery of function. For the forelimb placing test, all but one stem cell treated animal (9/10) did better than the mean of vehicle-treated animals by the end of the experiment. For the hindlimb placing test, all stem cell treated animals (10/10) did better than the mean of vehicle-treated animals by the end of the experiment.

No significant difference was observed in the swinging, cylinder, or paw reaching tests.

While the data show mixed results, sufficient improvement was observed in the forelimb and hindlimb placing tests to lead the inventors to believe that the invention is viable. The tests performed measure different aspects of sensorimotor recovery, and the forelimb and hindlimb placing tests may be the most sensitive to treatment effects. The inventors believe that the results of the other tests could perhaps be improved by administering a higher dosage of cells or by repeated administration; these tests have not been conducted to date.

Other embodiments are within the claims. For example, the cells may be derived from other blood-based, non-fetal and non-embryonic sources.

What is claimed is:

1. A method for treating a human patient suffering from cerebral palsy, said method comprising administering to said patient a composition comprising cells isolated from human umbilical cord blood (UCB), wherein said cells comprise human CD34+/−, Lin− cells, and wherein said administering results in a measurable improvement in said cerebral palsy in said patient.

2. The method of claim 1 further comprising concurrently with or following administration of said CD34+/−, Lin− cells administering a growth factor to said patient.

3. The method of claim 2, wherein said growth factor is selected from the group consisting of oncostatin M, FGF, neurotrophin, IGF, CNTF, EGF, TGF-beta, LIF, interleukins, PDGF, and VEGF.

4. The method of claim 1, wherein said CD34+/−, Lin− cells are allogeneic cells.

5. The method of claim 1, wherein said CD34+/−, Lin− cells are characterized as negative for expression of CD2, CD3, CD14, CD16, CD19, CD24, CD56, CD66b, and glycophorin A, and positive for expression of flk-1, CD45, CXCR4, and MDR.

6. The method of claim 1, wherein said method comprises administering a population of cells consisting of human CD34+/−, Lin− cells.

7. The method of claim 1, wherein said UCB administered to said patient systemically, intracerebrally, intracisternally, intracerebroventricularly, or intraparenchymally.

8. A method for treating a human patient suffering from cerebral palsy, said method comprising administering to said patient a composition comprising human CD34+/−, Lin− cells from human umbilical cord blood (UCB), wherein said CD34+/−, Lin− cells are separated from other mononuclear cells present in said UCB prior to said administering and wherein said administering results in a measurable improvement in said cerebral palsy in said patient.

9. The method of claim 8 further comprising concurrently with or following administration of said CD34+/−, Lin− cells administering a growth factor to said patient.

10. The method of claim 9, wherein said growth factor is selected from the group consisting of oncostatin M, FGF, neurotrophin, IGF, CNTF, EGF, TGF-beta, LIF, interleukins, PDGF, and VEGF.

11. The method of claim 8, wherein said CD34+/−, Lin− cells are allogeneic cells.

12. The method of claim 8, wherein said CD34+/−, Lin− cells are characterized as negative for expression of CD2, CD3, CD14, CD16, CD19, CD24, CD56, CD66b, and glycophorin A, and positive for expression of flk-1, CD45, CXCR4, and MDR.

13. The method of claim 8, wherein said method comprises administering a population of cells consisting of human CD34+/−, Lin− cells.

14. The method of claim 8, wherein said UCB is administered to said patient systemically, intracerebrally, intracisternally, intracerebroventricularly, or intraparenchymally.

15. The method of claim 1, wherein said CD34+/−, Lin− cells are autologous cells.

16. The method of claim 8, wherein said CD34+/−, Lin− cells are autologous cells.

* * * * *

UNITED STATES PATENT AND TRADEMARK OFFICE
CERTIFICATE OF CORRECTION

PATENT NO. : 8,337,833 B2
APPLICATION NO. : 12/778006
DATED : December 25, 2012
INVENTOR(S) : Morey Kraus et al.

It is certified that error appears in the above-identified patent and that said Letters Patent is hereby corrected as shown below:

In the Specification:

Column 2, Line 2, replace "*Instranigral*" with --*Intranigral*--;

Line 11, replace "teratacarcinomal" with --teratocarcinomal--.

In the Claims:

Column 10, Claim 7, replace "UCB administered" with --UCB is administered--.

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,337,833 B2  Page 1 of 1
APPLICATION NO. : 12/778006
DATED : December 25, 2012
INVENTOR(S) : Morey Kraus et al.

It is certified that error appears in the above-identified patent and that said Letters Patent is hereby corrected as shown below:

In the Specification:

Column 2, Line 2, replace "*Instranigral*" with --*Intranigral*--;

Line 11, replace "teratacarcinomal" with --teratocarcinomal--.

In the Claims:

Column 10, Line 1 (Claim 7, Line 1) replace "UCB administered" with --UCB is administered--.

This certificate supersedes the Certificate of Correction issued June 4, 2013.

Signed and Sealed this
Second Day of July, 2013

Teresa Stanek Rea
*Acting Director of the United States Patent and Trademark Office*